United States Patent [19]

Dunkhase et al.

[11] Patent Number: 4,565,786
[45] Date of Patent: Jan. 21, 1986

[54] METHOD FOR DETECTING MERCURY GAS

[75] Inventors: John A. Dunkhase, Golden; Ronald W. Klusman, Evergreen; James C. Fisher, Golden, all of Colo.

[73] Assignee: Earth Search, Inc., Golden, Colo.

[21] Appl. No.: 599,147

[22] Filed: Apr. 11, 1984

[51] Int. Cl.⁴ .................. G01N 1/22; G01N 33/20; G01N 33/24

[52] U.S. Cl. .................. 436/26; 73/863.12; 73/863.52; 73/864.51; 422/88; 436/25; 436/81; 436/178

[58] Field of Search ............ 436/25, 26, 28, 178, 436/81; 422/88; 73/863.51, 863.52, 864.51, 864.59, 863.11, 863.12

[56] References Cited

U.S. PATENT DOCUMENTS

| | | | |
|---|---|---|---|
| 3,593,583 | 7/1971 | Anderson et al. | 73/863.11 |
| 3,730,683 | 5/1973 | Milly | 436/26 |
| 3,852,604 | 12/1974 | Grengg | 436/81 X |
| 4,064,436 | 12/1977 | Ward, III . | |
| 4,065,972 | 1/1978 | Holub et al. . | |
| 4,156,138 | 5/1979 | Felice . | |
| 4,277,251 | 7/1981 | Leichnitz | 422/88 X |

FOREIGN PATENT DOCUMENTS 0146503  2/1981  Fed. Rep. of Germany ........ 436/81

OTHER PUBLICATIONS

Redhead, Vacuum, 12, 203 (1962).

Primary Examiner—Arnold Turk
Attorney, Agent, or Firm—Fields, Lewis, Pittenger & Rost

[57] ABSTRACT

A method and apparatus has been provided to locate a subterranian precious ore and/or sulfide body from which mercury gas is emanating. The apparatus includes an inverted plastic drinking cup from which a mercury-free silver wire is suspended from its end. This is accomplished by inserting the end of the wire into a foam insulation disk located in the bottom of the inverted cup. Alternatively, wire may be attached within a cap of a storage vial. The cap has an adhesive on the outer surface which adheres it to the bottom of the cup, whereupon the vial is removed from the cap to expose the wire. A foil disk is placed on the outside of the bottom of the cup. A plurality of cups are buried in the ground forming a dead air space around the wire, for a period of weeks wherein any mercury-vapor in the ground in the area of the cup is adsorbed by the wire. These cups are arranged in a predetermined array and are subsequently located by means of a metal detector which can detect the metal foil on the cups. Upon removal, the wires are placed in a clean vial and refrigerated until such time as the amount of mercury in the wires can be determined. This is accomplished by removing the wires from the vial and vaporizing the mercury by heating the wires to glowing and adsorbing the released mercury-vapor on a gold film in a Jerome Mercury Detector. The amount of mercury adsorbed by the respective wires is indicative of the size and location of the ore body.

4 Claims, 4 Drawing Figures

METHOD FOR DETECTING MERCURY GAS

TECHNICAL FIELD

This invention relates to a method of locating subterranean precious metal ore bodies and more particularly to a method and apparatus for doing so by means of mercury collection cups which are buried at predetermined locations above the expected ore body.

BACKGROUND ART

It is known in the prior art to bury inverted cups in a prearranged array for collecting gases for analyzing ore bodies therebelow. In this regard, U.S. Pat. No. 4,065,972 to Holub, et al. discloses attaching any one of a number of gas detectors to the inside bottom of a plastic drinking cup. The patent discloses that one such detector may be silver gauze for detecting mercury gas. These cups are buried in the earth at varying depths and left for a period of time for collecting the mercury gas or other specified gases that migrate from buried ore bodies through the earth and into the respective cups. After collection, the gas collected by the silver gauze or other collecting medium is analyzed by conducting a conventional atomic adsorption analysis.

U.S. Pat. No. 4,156,138 to Felice discloses suspending an alpha-sensitive dosimeter in an inverted cup between the bottom and open end to absorb alpha-radiation.

U.S. Pat. No. 4,064,436 to Ward III discloses a radon detector which includes an inverted cup with a detection strip which is sensitive to radon gas and also includes a pervious membrane across the mouth of the cup.

Although each of the prior art devices is satisfactory for its intended use, none of them discloses a method which provides extremely reliable results at minimal cost.

DISCLOSURE OF THE INVENTION

A method of detecting mercury gas emanating from a subsurface ore body containing precious metal and/or sulfides has been provided. The method includes suspending a length of mercury-free silver wire by one end from the inside bottom of an enclosure, such as an inverted plastic cup, and then burying a plurality of such cups in the ground in a predetermined array over an area suspected to contain the ore body. The enclosure forms a dead air space around the wire. The array of cups is left in the earth for a predetermined period of time to allow the silver wires to adsorb mercury vapor emitted from the ore body. Next, the cups are each located and removed from the earth and the amount of mercury adsorbed by the silver wires in each cup is determined to establish the location of anomalous concentrations of mercury gas which may aid in the discovery of the hidden ore bodies. Conveniently, the plastic cup can be in the shape of a frusto-cone having a piece of metal foil attached to the outside bottom of the cup and a piece of foam insulation attached to the inside bottom of the cup with the length of mercury-free silver wire suspended by one end from the foam insulation within the cup. The length of the wire is less than the height of the cup and when the cup is buried a dead air space is provided within the enclosure or cup with the silver wire suspended in the center thereof.

More particularly, the method includes heating the lengths of silver wire to temperature of 740° C. for several days to clean them and to render them mercury-free. These cleaned wires are then stored in an airtight vial prior to use. The wires are then each removed from their respective vials and suspended by one end from the inside bottom of an inverted plastic cup. Next, the cups are buried in the ground in a predetermined array over an area suspected to contain the ore body. The array of cups are left in the earth for a predetermined period of time to allow the silver wires to adsorb mercury vapor emitted from the ore body. The cups are then located by metal detection devices and removed from the earth. The silver wire is removed from each cup and stored in a separate airtight vial at refrigerated temperatures prior to determining the amount of mercury adsorbed in each wire. The silver wires are stored at a temperature of 20° C. or below. Each wire is subsequently removed from its vial and heated to vaporize the mercury from it into a Jerome Mercury Detector. Each cup can be washed for reuse. After the mercury has been removed and analyzed from each wire, the wires can be cleaned again for reuse, as outlined above.

A number of advantages accrue through the use of the foregoing method and apparatus over state of the art technology. This method provides an accurate geochemical indication of hidden ore bodies and may identify those ore bodies hidden at depth. It is easily applied in the field and does not require special equipment or specially trained field personnel. It also eliminates the need to carry bulky soil or rock samples. In addition, it is sensitive to very low mercury levels. In this regard, the analysis is reproducibly sensitive to 0.05 nanograms of mercury. This method eliminates meteorological interferences, such as air and soil temperature, soil moisture and barometric pressure, which effects mercury-vapor in the soil and in the air. The method eliminates the analytical interferences from organic matter which occur when analyzing mercury in soils. It works well in all types of soil and under any vegetation cover. It has no significant effect on the environment and eliminates spurious anomalies which are unrelated to mineralization.

Additional advantages of this invention will become apparent from the description which follows taken in conjunction with the accompanying drawings.

BEST MODE FOR CARRYING OUT THE INVENTION

Figure 1:
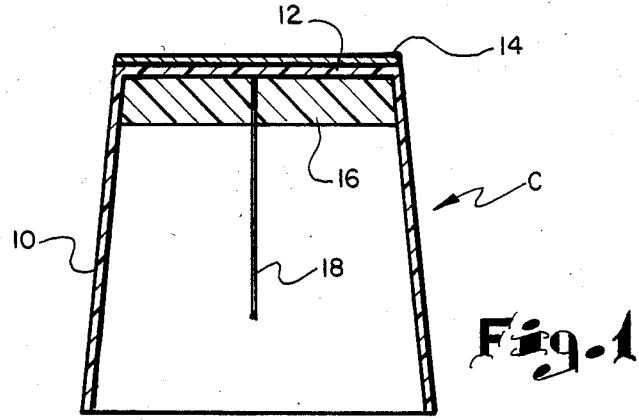
FIG. 1 is a vertical section through a mercury cup constructed in accordance with this invention showing the arrangement of the silver wire therein.

In accordance with this invention an enclosure, such as a mercury cup C, is provided, as best seen in FIG. 1. The cup may be of frusto-conical configuration which is used in inverted position as shown. The cup can be a standard plastic drinking cup having a base or bottom of approximately two inches in diameter and a height of about three and a half inches and a mouth approximately two and a half inches wide. The cup has tapered sidewalls 10 which are formed integrally with bottom 12. It will be understood, that although a plastic cup has been illustrated and described, any suitable enclosure which will provide a dead air space can be utilized. Thus, by way of illustration, the enclosure might be a glass jar, a funnel shaped device, an aluminum cup or can.

On the outside of bottom 12 a layer of metal foil 14 is provided to serve as a means by which the cup can be located after it is buried. Conveniently, foil layer 14 can be attached to bottom 12 by any suitable means, such as by adhesive. On the inside of the cup a disk 16, made of plastic foam insulating material is provided. A suitable fiberglass insulating material is Thermex, manufactured by Cellotex. This may be of such size as to frictionally engage the sidewalls 10 of the cup and be held in place or it can also be held in place by a suitable adhesive against the inside of cup bottom 12. A length of mercury-free silver wire 18 is suspended in the center of the cup. A suitable wire is #18 gauge analytical grade silver, having a purity of 99.5% to 99.8%. This is accomplished by inserting one end of wire 18 into foam disk 16 at or near the center thereof. As mercury-vapor moves up from the ore body it will be adsorbed on the silver wire 18 within the mercury cup.

Although a silver wire has been described, it will be understood that the material can be any precious amalgamating substance. By way of example such a substance can be silver or gold wires, meshes or sponges.

The first step in the process is to thoroughly clean each wire 18 to assure that it is free of any residual mercury. This can be done by heating it to 740° C. for 72 hours, such as in a muffle furnace 20 diagramatically illustrated in FIG. 2. The wire should subsequently be tested analytically to verify that it is free of mercury and then each of these clean wires can then be stored in an airtight plastic vial 22 for transportation to the field.

In the field, the wires 18 can each be removed from their respective vials 22 and inserted in disk 16 of cup C. The assembled mercury cups are then placed in a predetermined array, as in a grid pattern 24 in the area of mineralogical interest at a shallow depth. At the site where each cup is to be placed, a hole is dug, which is between six inches and one foot from the surface. The cups are placed upside down (with open end down). No dirt is allowed to fill the cups or to come in contact with the wires. Each cup forms a dead air space around the wire which it contains. The soil is lightly repacked over each cup. Caution is taken to be sure that the pressure applied to the soil is not so great as to cause the cups to become cracked. On the other hand, the soil should be sufficiently packed so that there will not be sufficient settling or packing of the soil above the cup to expose or identify the location. It is desirable to return the ground surface of the cup site to its normal appearance after burial of each cup by spreading rocks, sticks and leaves over the disturbed area. The spacing of the cups can vary from 20 to 1,000 feet but a spacing distance of approximately 150 feet has been normally found to be satisfactory. For vein-type mineralization, the mercury cups are closely spaced along traverses. The distance between traverses is dependent upon the suspected width of the veins. The mercury cup traverses are directed normal to the suspected structural trends. For desseminated type mineralization, the mercury cups are set at a widely spaced grid pattern. The spacing depends upon the suspected size and geometry of the ore body.

The traverse lines of the mercury cups can be located on the surface by setting survey stakes along the line at desired spacing. In order to prevent the mercury cup locations to be identified by any unauthorized personnel, the cups are normally planted at a predetermined offset from the survey line. Additionally, the cups are not planted adjacent their respective stakes, but instead each cup is planted at a distance from its stake in a specified direction. With the aid of a metal detector, and instructions identifying the specific location of each cup, authorized personnel will be able to successfully retrieve them. Naturally, the foil layer 14 on the top of each cup makes it possible to detect the cups in this manner.

The mercury cups are normally allowed to remain in the ground for six to eight weeks. This exposure period is dependent upon the climate of the field site and the time of year. Cooler temperatures require more time to develop a mercury signal representative of the subsurface geochemistry.

The array of cups C, as discussed above, can be located by means of flags 26 and the use of metal detectors.

Figure 2:
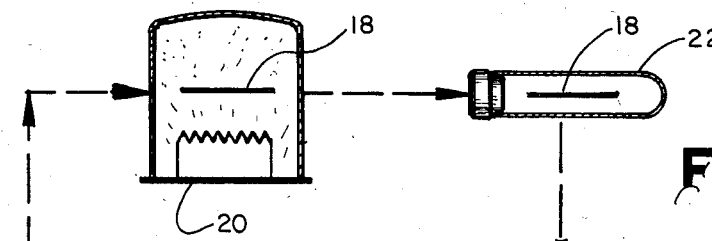
FIG. 2 is a diagram illustrating the method of this invention.
Figure 2:
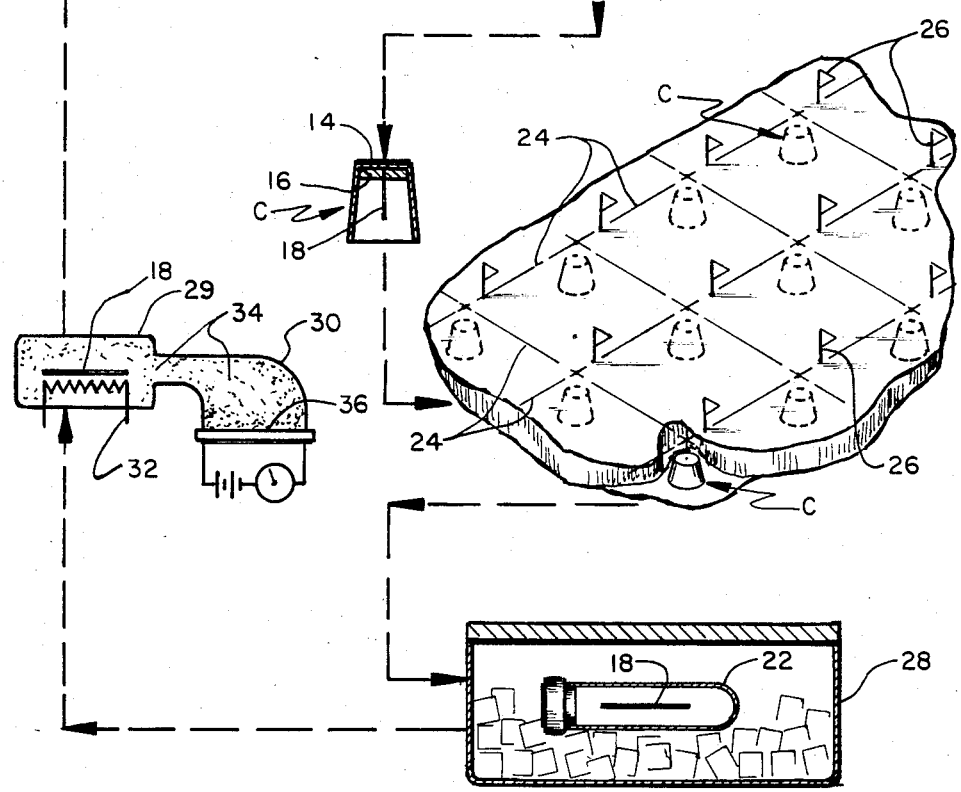

During and subsequent to retrieval of the mercury cups, the exposed silver wires must be kept cold and dry. After each buried cup is located and unearthed, the silver wire is removed from the cup with pliers and stored in a labeled vial. The labeling on each vial corresponds to the location of the wire when it was buried. The lid for the vial should fit tightly to prevent mercury loss from the wire or contamination of the wire from extraneous sources of mercury. The exposed wires should be stored at a low temperature of 20° C. or below to prevent distortion of the adsorbed mercury signal. The vials can be stored in a suitable ice chest 28 as shown in FIG. 2 or in a refrigerated van or other suitable refrigeration means. Care must be taken when using ice to prevent the melting ice from coming into contact with the exposed wire since this may result in the adsorbed mercury dissolving. Frozen packets of "Blue Ice" can be used effectively because they will maintain low temperatures in an ice chest but are well sealed so as not to create leakage problems. By maintaining the wires sealed in plastic vials and by keeping them cold and dry, the analysis for mercury need not be conducted immediately. Exposed silver wires have been stored in a freezer for one month and still provide strong representative signals when analyzed.

The exposed silver wires are analyzed by vaporizing the adsorbed mercury from the wire and drawing the vapor into a Jerome Mercury Detector. Each silver wire 18 is placed into a quartz combustion tube 29 which is inserted into the air flow path of the mercury detector 30. The combustion tube then is heated to glowing for 60 seconds with a heating element 32. Mercury-vapor 34 is drawn from the combustion tube into the mercury detector 30, which may be a Jerome Mercury Detector Model #301, which absorbs to a thin gold film 36 in the detector. The change in the electrical resistance of the gold film, as mercury amalgamates to it, measures the apparent mercury concentration.

Conversion of each mercury detector reading into a mercury concentration value requires calibration of the mercury detector. The calibration procedure involves the injection of a specific volume of mercury-vapor from a dewar into the flow-path of the mercury detector and the recording of the observed detector readings. For a constant and known temperature, the specific volume of mercury-vapor contains a specific weight of gaseous mercury. The mercury-vapor which is injected into the mercury detector is withdrawn from the sealed dewar containing a drop of liquid mercury. The liquid mercury in the dewar is equilibrated with the air filling the dewar. This liquid-vapor equalization results in a constant partial pressure of mercury in the dewar for each specific temperature. By plotting the weights of the injected mercury against the respective detector readings, the resulting calibration curve can be used to convert mercury detector values into mercury concentration. After the mercury has been vaporized from wire 18, the wire may go back to the muffle furnace 20 for thorough cleaning and placement in a clean vial 22 for reuse. The used cups can be rewashed for subsequent use with another clean wire.

Figure 3:
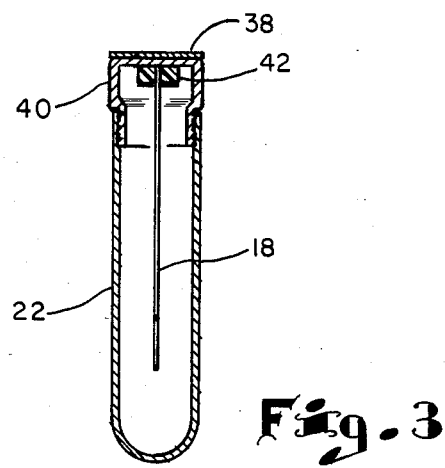
FIG. 3 is a side elevation of a specially constructed vial for holding a silver wire and for supporting it when being exposed to mercury gas.
Figure 4:
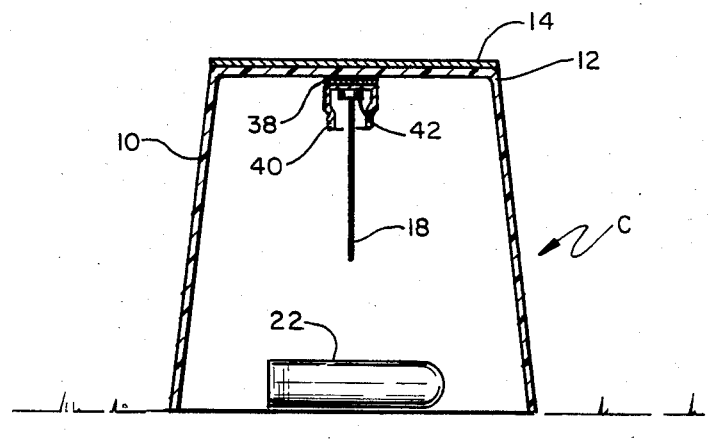
FIG. 4 is a side elevation of a cup showing the use of the cap of the vial of FIG. 3 to support the silver wire.

An alternative arrangement of suspending the silver wire 18 from the interior of cup 10 is illustrated in FIGS. 3 and 4. Conveniently, an adhesive layer 38 is attached to the outside top surface of cap 40 of vial 22. The silver wire 18 is suspended from a foam disk 42 which is glued or otherwise attached to the interior top surface of cap 40.

At the site, the vial with cap attached is secured to the inside of bottom 12 of cup C by the adhesive 38. The vial 22 is then unscrewed from cap 40 to expose the wire. If desired, the vial 22 can be laid on the ground under the cup so that upon retrieval, it will easily be found. When the cup is dug up, the vial 22 is again placed over silver wire 18 and threaded onto cap 40 whereupon the vial and cap are pulled from the cup and stored as before, such as in ice chest 28.

From the foregoing, it can be seen that a very simple yet efficient method of detecting mercury-vapor and thereby identifying mineral ore bodies has been provided. This method can be conducted without adversely impacting the ecology of the area. Its utility does not required skilled personnel and the equipment is inexpensive and reusable.

It will be understood that this invention can be used for detecting mercury gases for other reasons then to locate precious metal ore bodies. For example, it can be used anywhere that the detection of mercury gas gives an indication of a condition of interest, such as for geothermal monitoring, petroleum monitoring and environmental monitoring.

The invention has been described in detail with particular reference to preferred embodiments thereof, but it will be understood that variations and modifications can be effected within the spirit and scope of the invention.

What is claimed is:

1. A method of detecting mercury gas emanating from a subsurface ore body containing precious metal or sulfides, said method comprising the steps of:

heating lengths of silver wire to a sufficient temperature for a sufficient length of time to clean them and to render them mercury free;

attaching one end of each wire to the inside of a removable vial cap;

attaching each cap to the top of a vial with the wire suspended from the cap therein;

transporting the silver wires in the vials to a test area;

removing each cap and attached wire from each vial and attaching the outside of each cap to the inside bottom of an inverted plastic cup without touching the wire so that the wire is suspended by each cap inside of each cup;

burying a plurality of the cups to which a cap and wire has been attached to each in the ground in a predetermined array over an area suspected to contain the ore body;

leaving said array of cups in the earth for a predetermined period of time to allow the silver wires to adsorb mercury-vapor emitted from the ore body;

locating each cup in the array and removing it from the earth;

removing the cap with attached silver wire from each cup after the cup is removed from the earth without touching the wire;

reattaching each cap to each vial with a silver wire still suspended from each cap to form an airtight enclosure for each silver wire;

refrigerating each vial and silver wire so that any mercury adsorbed on the silver wires will remain therein;

storing each vial and wire at refrigerated temperature prior to determining the amount of mercury adsorbed in each wire; said subsequently removing each wire from its refrigerated vial and heating it to vaporize the mercury from it; and measuring the amount of mercury removed from each wire.

2. A method, as claimed in claim 1, wherein: each silver wire and vial is stored at a temperature of 20° C. or below.

3. A method, as claimed in claim 1, wherein the first heating step includes:

removing naturally occuring mercury from each silver wire prior to use by heating each wire to a temperature of 740° C. for several days.

4. A method, as claimed in claim 1, including the further steps of:

placing a piece of metal foil on the outside of each cup prior to burying;

locating the cups for removing them from the earth by means of a metal detector.

* * * * *